US010064992B2

(12) United States Patent
Yang

(10) Patent No.: US 10,064,992 B2
(45) Date of Patent: Sep. 4, 2018

(54) DISPOSABLE TUBELESS FLUID DELIVERY SYSTEM

(71) Applicant: MEDTRUM TECHNOLOGIES INC., Shanghai (CN)

(72) Inventor: Cuijun Yang, Shanghai (CN)

(73) Assignee: Medtrum Technologies Inc. (CN)

( * ) Notice: Subject to any disclaimer, the term of this patent is extended or adjusted under 35 U.S.C. 154(b) by 0 days.

(21) Appl. No.: 14/897,702

(22) PCT Filed: Oct. 15, 2014

(86) PCT No.: PCT/CN2014/088615
§ 371 (c)(1),
(2) Date: Dec. 11, 2015

(87) PCT Pub. No.: WO2016/033854
PCT Pub. Date: Mar. 10, 2016

(65) Prior Publication Data
US 2016/0199572 A1 Jul. 14, 2016

(30) Foreign Application Priority Data

Sep. 3, 2014 (CN) .......................... 2014 1 0446153

(51) Int. Cl.
*A61M 5/142* (2006.01)
*A61M 5/172* (2006.01)
*A61M 5/158* (2006.01)

(52) U.S. Cl.
CPC .... *A61M 5/14276* (2013.01); *A61M 5/14248* (2013.01); *A61M 5/172* (2013.01);
(Continued)

(58) Field of Classification Search
CPC .... A61M 5/14248; A61M 2005/14208; A61M 2005/14268; H01R 13/5202
See application file for complete search history.

(56) References Cited

U.S. PATENT DOCUMENTS 4,755,173 A * 7/1988 Konopka .......... A61M 25/0606
128/DIG. 26
6,752,787 B1 * 6/2004 Causey, III ....... A61M 5/14566
604/131

(Continued)

FOREIGN PATENT DOCUMENTS

CN 102688539 A 9/2012
CN 103083751 A 5/2013
(Continued)

OTHER PUBLICATIONS

Patek et al., "Modular Closed-Loop Control of Diabetes", IEEE Transactions on Biomedical Engineering, Nov. 2012, vol. 59, No. 11, 2986-2999.

*Primary Examiner* — Andrew Gilbert
*Assistant Examiner* — John Doubrava
(74) *Attorney, Agent, or Firm* — Baker & Hostetler LLP

(57) ABSTRACT

Disclosed is a disposable tubeless fluid delivery system, comprising a button unit for receiving instructions given by a user through pressing button, a key unit for outputting a selection instruction indicating at least one working mode a fluid reservoir unit for storing a fluid, an indwelling unit for letting through the fluid to a patient, wherein the indwelling unit comprises an indwelling cannula, and a fluid driving unit for delivering the fluid stored in the fluid reservoir unit to the subcutaneous tissue of the patient by the indwelling unit, and a control unit for outputting the delivery instruction to the fluid driving unit and controlling the fluid driving unit to deliver the fluid or suspend fluid delivery. In the present disclosure, a pump base and a wireless control device are integrated to achieve a purpose of small volume, low cost and convenient wearing.

22 Claims, 13 Drawing Sheets

(52) U.S. Cl.
CPC . *A61M 5/1723* (2013.01); *A61M 2005/14208* (2013.01); *A61M 2005/1586* (2013.01); *A61M 2205/18* (2013.01); *A61M 2205/35* (2013.01); *A61M 2205/3569* (2013.01); *A61M 2205/502* (2013.01); *A61M 2205/582* (2013.01); *A61M 2230/005* (2013.01); *A61M 2230/201* (2013.01)

(56) References Cited

U.S. PATENT DOCUMENTS

| | | | | |
|---|---|---|---|---|
| 7,547,218 | B2* | 6/2009 | Hiew | H01R 13/6395 439/135 |
| 8,747,348 | B2* | 6/2014 | Yodfat | A61M 5/14248 604/131 |
| 8,915,879 | B2* | 12/2014 | Smith | A61M 5/145 604/152 |
| 2006/0122577 | A1* | 6/2006 | Poulsen | A61M 5/1413 604/890.1 |
| 2008/0086086 | A1 | 4/2008 | Field et al. | |
| 2009/0069785 | A1 | 3/2009 | Miller et al. | |
| 2010/0261367 | A1* | 10/2010 | Billman | H01R 13/622 439/271 |
| 2011/0009824 | A1* | 1/2011 | Yodfat | A61M 5/14248 604/151 |
| 2013/0060225 | A1* | 3/2013 | Wenger | A61M 5/14244 604/500 |
| 2013/0338598 | A1* | 12/2013 | Gyrn | A61M 5/14248 604/174 |
| 2015/0244101 | A1* | 8/2015 | Chien | H01R 13/5202 439/271 |

FOREIGN PATENT DOCUMENTS

| | | |
|---|---|---|
| CN | 103083756 A | 5/2013 |
| CN | 203227106 U | 10/2013 |
| CN | 103585689 A | 2/2014 |
| WO | WO 2004/041330 A2 | 5/2004 |
| WO | WO 2006/049446 A1 | 5/2006 |
| WO | WO 2009/016635 A2 | 2/2009 |
| WO | WO 2014/029416 A1 | 2/2014 |

* cited by examiner

DISPOSABLE TUBELESS FLUID DELIVERY SYSTEM

CROSS-REFERENCE TO RELATED APPLICATIONS

The present application is a Section National Stage Application of International Application No. PCT/CN2014/088615, filed on Oct. 15, 2014, which claims priority to Chinese patent application No. 201410446153.9, filed on Sep. 3, 2014, and entitled "DISPOSABLE TUBELESS FLUID DELIVERY SYSTEM", the entire disclosure of which is incorporated herein by reference.

TECHNICAL FIELD

The present disclosure generally relates to the field of medical appliance, and more particularly, to a disposable tubeless fluid delivery system configured to continuously infuse deliver therapeutic liquids into a patient.

BACKGROUND

A fluid delivery device is a medical appliance which can achieve patient disease treatment by continuously delivering a fluid into the patient. The fluid delivery device is widely used in the treatment of diabetes. The fluid delivery device continuously delivers insulin to a subcutaneous tissue of a patient based on a dosage required by the patient, so as to simulate the secretion function of the pancreas and stabilize glucose of the patient. The fluid is usually stored in a pump base, and a conventional fluid delivery device usually delivers the fluid into a patient via a catheter connected to the pump base. The catheter, when it is used, is not only an obstruction for the patient's activities, but also not beautiful.

In order to overcome the above-mentioned shortcomings of the conventional fluid delivery device, a tubeless fluid delivery device has been developed, which has a pump base stuck to the patient's body by a medicine adhesive plaster, and an indwelling cannula implanted in a subcutaneous tissue of the patient to deliver a fluid. The tubeless fluid delivery device integrates the pump base and a control module in a box, and remotely control and administrate drug delivery by a wireless handheld device. However, the patient is required to wear the pump base and carry the wireless handheld device, at the same time, when the patient is being treated by the existing tubeless fluid delivery device. The existing tubeless fluid delivery device has some shortages such as radio interference and high costs. Moreover, the existing tubeless fluid delivery device has some shortcomings of complicated operation, large size, large mass, and inconvenient wearing.

A normal pancreas may automatically monitor the changes of glucose, and may automatically secrete insulin required. "Real time dynamic glucose monitoring system" indicates a device that can real-timely and dynamically monitor the changes of glucose by using a glucose sensor implanted in the subcutaneous tissue of a patient. Considering the comfort level of patients when they are wearing these components, the indwelling cannula implanted in a subcutaneous tissue of a patient and the glucose sensor implanted in a subcutaneous tissue of a patient are both made of slender and soft medical polymer materials. Because of the special nature of the materials and the shapes of the two discrete components, they both need to be put into the subcutaneous tissue of a patient with a help of a puncture needle with a certain rigidity to puncture the skin of the patient. Thereafter, the needle is pulled out, leaving the two components in the subcutaneous tissue. The glucose sensor and the indwelling cannula have similar processes of puncture and indwelling. Moreover, the glucose sensor and the indwelling cannula are also the same in the aspects such as area of action on body, disposable using, aseptic production, etc.

SUMMARY

Regarding the above-mentioned shortcomings of the prior art, an object of the present disclosure is to provide a disposable tubeless fluid delivery system for solving the problems such as large size, high costs, complex components, and inconvenient wearing, where the disposable tubeless fluid delivery system integrates a pump base and a wireless control device, and is easy to use.

In order to achieve the above-mentioned purposes and other related purposes, the present disclosure provides a disposable tubeless fluid delivery system, including: a button unit configured to receive instructions given by a user through pressing button; a key unit configured to output a selection instruction indicating at least one working mode, wherein the at least one working mode is selected from a group consisting of a basal rate delivery mode, a programmable basal rate delivery mode, an delivery suspend mode, a system locking mode and a wireless control mode; a fluid reservoir unit configured to store a fluid; an indwelling unit configured to let through the fluid to a patient when it is implanted in a subcutaneous tissue of the patient, wherein the indwelling unit includes an indwelling cannula configured to be implanted in the subcutaneous tissue of the patient; a fluid driving unit configured to deliver the fluid stored in the fluid reservoir unit to the subcutaneous tissue of the patient via the indwelling unit, when it receives an delivery instruction; and a control unit coupled to the button unit, the key unit, the fluid reservoir unit, the indwelling unit and the fluid driving unit, wherein the control unit is configured to, when it receives a button-pressing instruction, the selection instruction of the working mode, or a combination thereof, output the corresponding delivery instruction to the fluid driving unit, so as to control the fluid driving unit to deliver the fluid or suspend fluid delivery.

Optionally, the button unit includes physical buttons, touch buttons, or a combination thereof, where the physical buttons include a first physical button configured to set fluid dose, and a second physical button configured to input a confirmation instruction, one of the physical buttons is provided with raised dots to be distinguished with the other physical button.

Optionally, the key unit includes a key and a socket, and the key further includes a handle configured to combine and separate the key and the socket.

In some embodiments, the key includes a key shell, a built-in electric circuit located inside the key shell, and a plug embedded in the key shell. An O-shaped sealing ring is circumferentially set on the key shell. The built-in electric circuit is an analog circuit including electric resistances, electric capacities or a combination thereof, or a digital integrated circuit including Flash, EEROM, or one-time DATA BURNING type memory device, or a digital integrated circuit with identity recognition function, or a digital integrated circuit with an authentication function, an encryption function or a combination thereof, or a digital-analog hybrid integrated circuit. The socket includes a slot and a connector set in the slot. The connector is used to be electrically connected with the built-in electric circuit when the key is inserted into the socket. An O-shaped sealing ring is set on the surface on which the connector is attached with the socket. The plug is inserted into the connector and thus electrically connected with the connector, when the key is inserted into the socket. The O-shaped sealing ring on the key shell and the socket fit tightly to achieve waterproof seal.

In some embodiments, the socket is a sealed groove, and the key is a sensing key which includes a key shell and a sensor circuit located in the key shell. The sensor circuit includes a magnetic sensor, an optical sensor, a near field communication (NFC) tag or a radio frequency identification (RFID) tag.

Optionally, a buzzer cavity is set in a shell of the disposable tubeless fluid delivery system. A buzzer is set in the buzzer cavity, where the buzzer is configured to produce a buzz to sound an alarm, a reminder, or a combination thereof, and the buzzer is also configured to transmit ultrasonic data. The buzzer is connected to the control unit via a wire or a contact.

Optionally, a groove is set in a shell of the disposable tubeless fluid delivery system and a vibration motor is disposed in the groove, where the vibration motor is connected to the control unit via a wire.

Optionally, the disposable tubeless fluid delivery system further includes an indicator light, a transparent portion is correspondingly set on a shell of the disposable tubeless fluid delivery system, such that the indicator light indicates a system state by flashing through the transparent portion.

Optionally, the disposable tubeless fluid delivery system further includes a glucose sensor configured to dynamically monitor glucose level and a glucose monitoring module configured to process effective glucose signals output by the glucose sensor, wherein the glucose sensor is integrated in the indwelling unit, the glucose monitoring module is integrated in the control unit connected to the indwelling unit.

Optionally, the disposable tubeless fluid delivery system includes a controller and a pump base connected to the controller, where the control unit, the button unit and the key unit are set on the controller, and the fluid reservoir unit and the indwelling unit are set on the pump base.

As is mentioned above, the disposable tubeless fluid delivery system provided in the present disclosure uses independent control structure to enhance convenience of using and wearing. That is, the control unit, the button unit and the key unit are set in one device, where the control unit is configured to process an instruction given by a user, and coordinate and manage the device operation, while the button unit and the key unit are configured to realize communications between the user and the device. Furthermore, setting the button and the key on the device realizes the fluid delivery and completes treatment for a patient under the cooperations of the buzzer, the vibration motor and the indicator light. In some embodiments, the indwelling unit is combined with the glucose sensor, and the control unit is combined with the glucose monitoring module. As such, the disposable tubeless fluid delivery system can realize both glucose monitoring and fluid delivery, so as to complete treatment for the patient. Specifically, when the patient is being treated, he/she sticks the whole device to his/her skin, and sets up a program of fluid delivery by the button unit and/or the key unit. In response to the user's instruction, or when the fluid stored in the pump base runs out, or the device breaks down, the disposable tubeless fluid delivery system will remind the user to do the next step operation by using the buzzer, the vibration motor, the indicator light, or a combination thereof.

DETAILED DESCRIPTION OF THE DISCLOSURE

Figure 1:
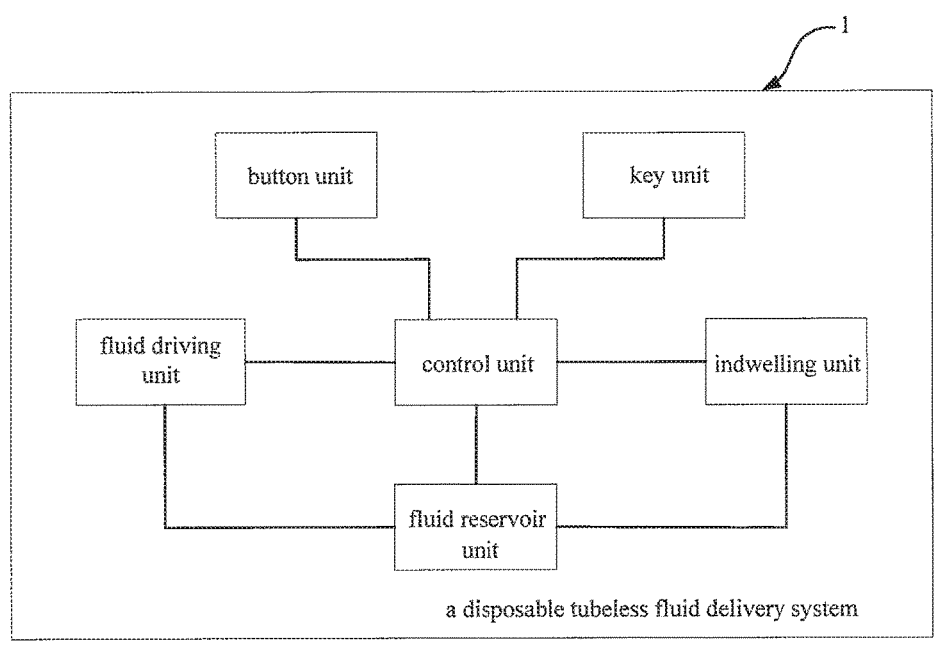
FIG. 1 illustrates a block diagram of a disposable tubeless fluid delivery system in the present disclosure.

The embodiments of the present disclosure are described in the following through specific examples, and those skilled in the art can easily understand other advantages and effects of the present disclosure according to the content disclosed in the specification.

Referring to the FIG. 1 to FIG. 17, it should be noted that, the structures, the scales, the sizes, like shown in the drawings, are only used to match the content disclosed in the specification, for being understood and read by those skilled in the art, instead of limiting limited implementation conditions of the present disclosure, and thus not have any essential technical meaning. Any modification in structure, change in scale, or adjustment in size should fall within the scope of the technical content disclosed by the present disclosure without influencing the generated efficacy and achieved objective of the present disclosure. Meanwhile, some words such as "upper", "lower", "left", "right", "middle", and "a" quoted in the specification are only used for clarity of the illustration instead of limiting the implementation scope of the present disclosure, and any change or adjustment of relative relationships should be considered as falling within the scope of implementation of the present disclosure without essentially changing the technical content.

The present disclosure provides a disposable tubeless fluid delivery system configured to achieve a patient disease treatment by continuously delivering a fluid into the patient. In actual practice, the fluid delivery device is widely used in the treatment of diabetes. The fluid delivery device continuously delivers insulin to a subcutaneous tissue of the patient based on a dosage required by the patient, and then simulates the secretion function of pancreas and stabilizes glucose of the patient. Referring to FIG. 1, a block diagram of a disposable tubeless fluid delivery system in the present disclosure is illustrated. As shown in FIG. 1, the disposable tubeless fluid delivery system includes a button unit, a key unit, a fluid reservoir unit, an indwelling unit, a fluid driving unit and a control unit.

Figure 2:
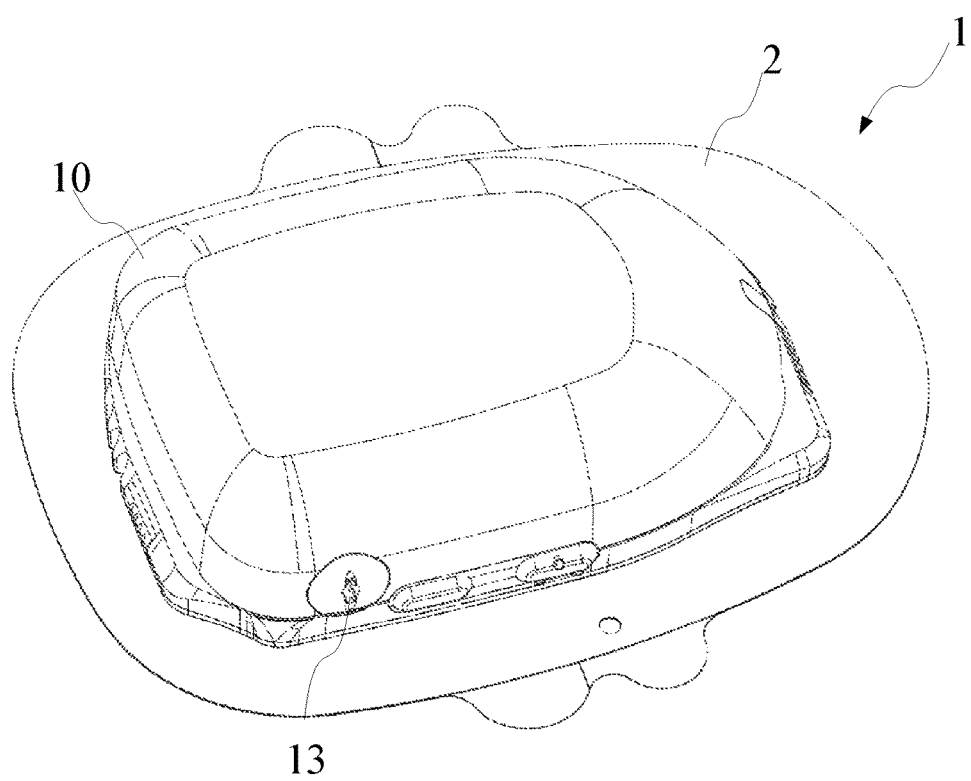
FIG. 2 illustrates a schematic diagram of a disposable tubeless fluid delivery system in the present disclosure, where all components are integrated in a box or shell.

In some embodiments, the disposable tubeless fluid delivery system 1 may integrate the button unit, the key unit, the indwelling unit, the fluid driving unit and the control unit in a box or a shell 10. Referring to FIG. 2, a schematic diagram of a disposable tubeless fluid delivery system in the present disclosure is illustrated, where all components are integrated in a box or shell.

Figure 3:
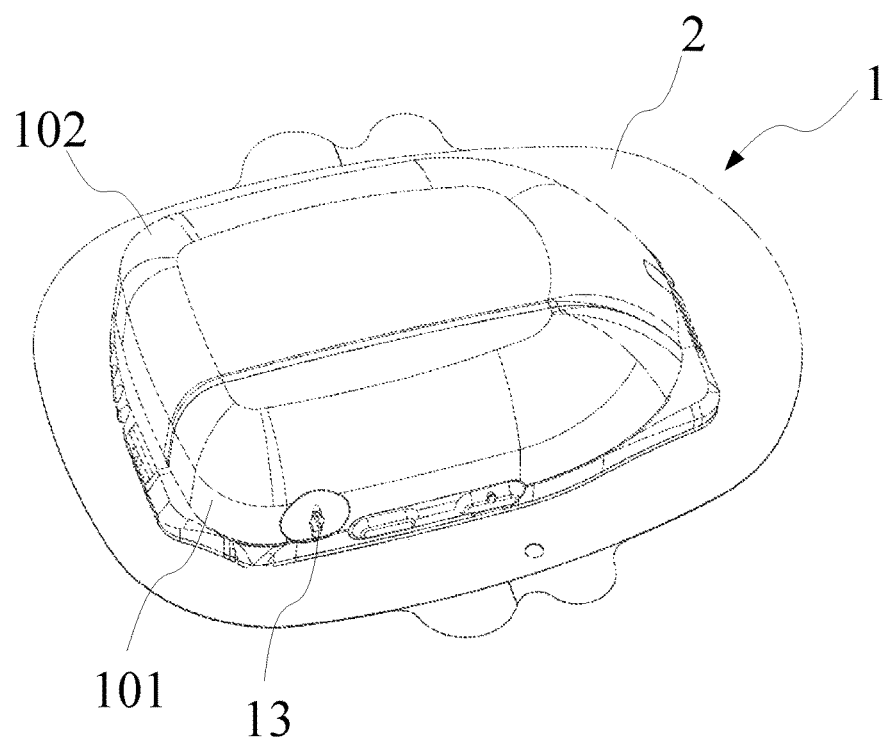
FIG. 3 illustrates a schematic diagram of a disposable tubeless fluid delivery system in the present disclosure, where a pump base and a controller are separable components.

In some embodiments, the disposable tubeless fluid delivery system 1 includes a controller 101 and a pump base 102 connected to the controller 101 or separated from the controller 101. The control unit, the button unit and the key unit are set on the controller 101. The fluid reservoir unit, the fluid driving unit and the indwelling unit are set on the pump base 102. Referring to FIG. 3, a schematic diagram of a disposable tubeless fluid delivery system in the present disclosure is illustrated, where a pump base and a controller are separable components.

Figure 4:
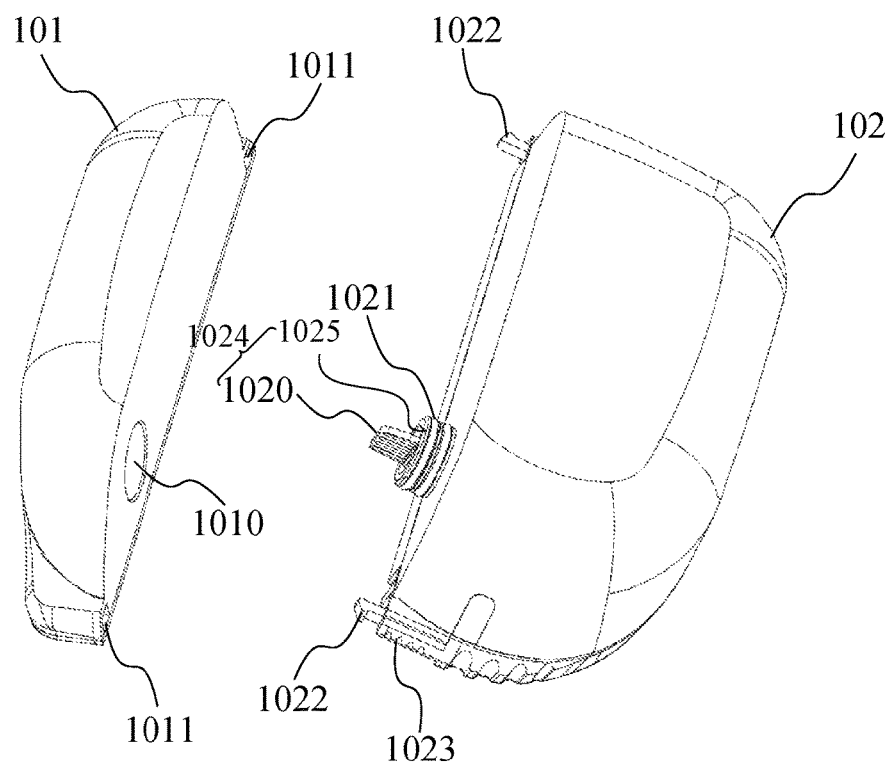
FIG. 4 illustrates a separated a controller and a pump base of a disposable tubeless fluid delivery system according to an embodiment of the present disclosure.

Referring to FIG. 4, a separated a controller and a pump base of a disposable tubeless fluid delivery system according to an embodiment of the present disclosure is illustrated. As shown in FIG. 4, when the disposable tubeless fluid delivery system 1 includes the controller 101 and the pump base 102, the pump base 102 and the controller 101 are combined by a snap hook socket or a third groove 1011 set on the controller 101 and a snap hook 1022 set on the pump base 102, and electrically connected by a second socket 1010 set on the controller 101 and a second plug 1024 set on the pump base 102. In some embodiments, the snap hook 1022 is connected to a snap hook handle 1023, and the snap hook 1022 may separate from the snap hook socket or the third groove 1011 by operating the snap hook handle 1023.

Figure 5:
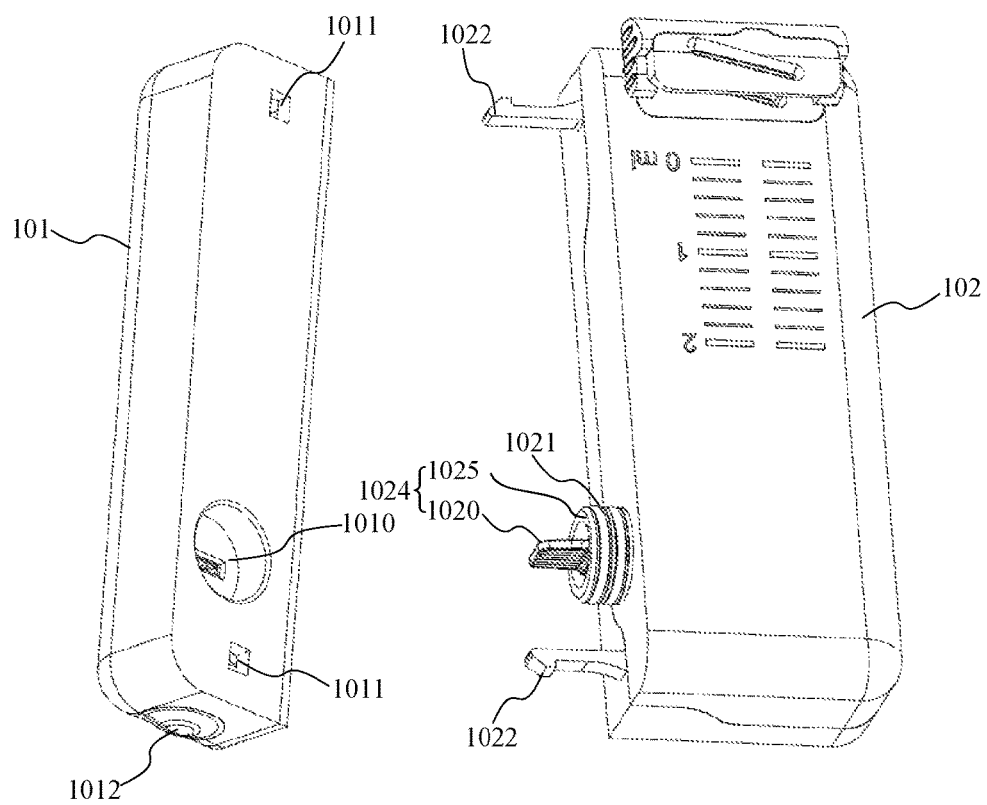
FIG. 5 illustrates a separated a controller and a pump base of a disposable tubeless fluid delivery system according to another embodiment of the present disclosure.

In some embodiments, referring to FIG. 5, a separated a controller and a pump base of a disposable tubeless fluid delivery system according to another embodiment of the present disclosure is illustrated. As shown in FIG. 5, a releasing key is set on the shell of the controller 101, where the releasing key is configured to separate the snap hook 1022 and the snap hook socket or the third groove 1011.

Figure 6:
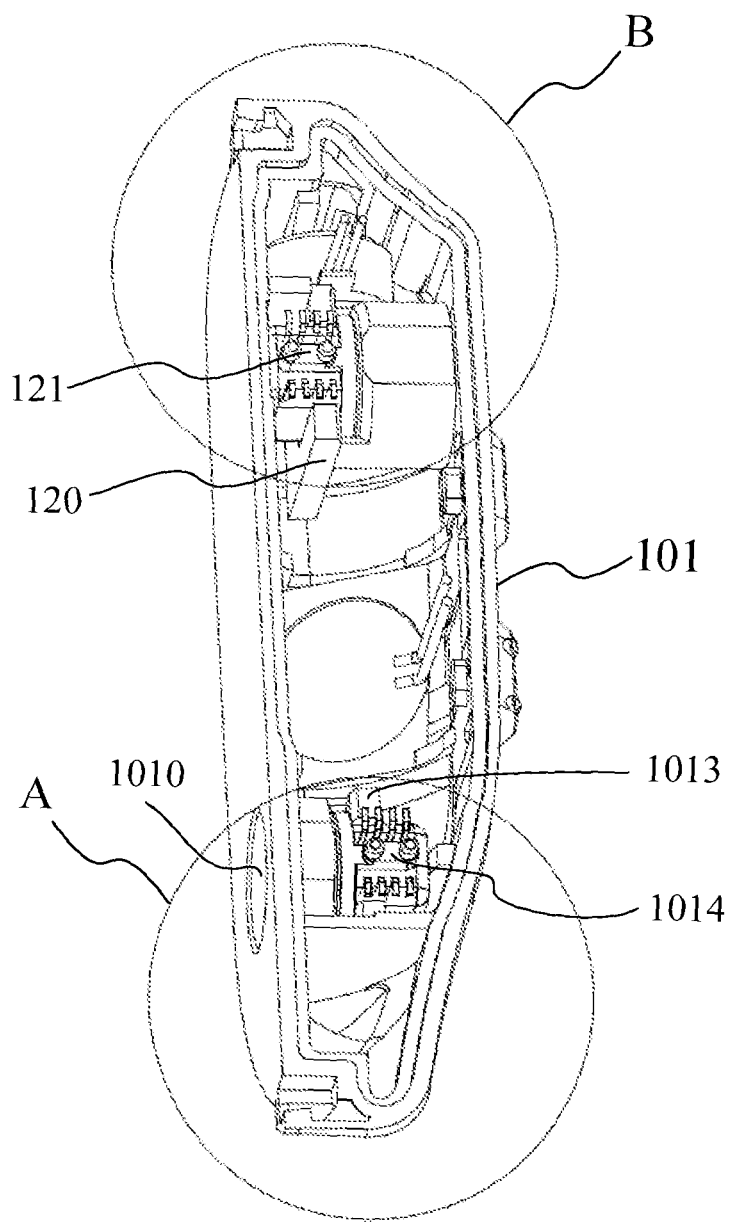
FIG. 6 illustrates an internal portion of a shell of a controller.
Figure 7:
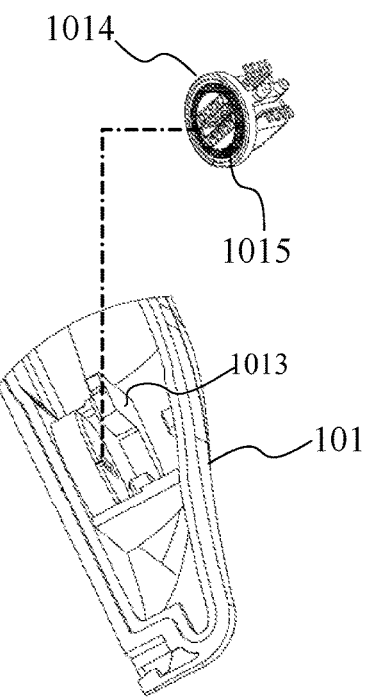
FIG. 7 illustrates an enlarged view in section on A of FIG. 6.

Referring to FIG. 6 and FIG. 7, an internal portion of a shell of a controller is illustrated, and an enlarged view in section on A of FIG. 6 is illustrated. As shown in FIG. 6 and FIG. 7, a connector position groove 1013 is set in the second socket 1010, a second connector 1014 is set in the connector position groove 1013, where the second connector 1014 is configured to be electrically connected to the control unit, a third O-shaped sealing ring 1015 is set on a fitting surface of the second connector 1014 and the second socket 1010.

As shown in FIG. 4 and FIG. 5, the second plug 1024 includes a plug body 1025 with a fourth O-shaped sealing ring 1021 and a plug end 1020 embedded in the plug body 1025, when the second plug 1024 is inserted into the second socket 1010, the plug end 1020 is inserted into the second connector 1014 and electrically connected with the second connector 1014, where the fourth O-shaped sealing ring 1021 on the plug body 1025 and the second socket 1010 fit tightly to achieve waterproof seal.

The button unit configured to receive instructions given by a user through pressing button. In some embodiments, the button unit includes physical buttons, touch buttons, or a combination thereof. The instructions are some instructions given by the user through pressing button, for example, opening, closing and restarting. Alternatively, a combined key is used to realize some instructions such as system infusion suspending, system hibernating and system programming.

In some embodiments, the physical buttons include a first physical button configured to set fluid dose, and a second physical button configured to input a confirmation instruction, one of the physical buttons is provided with raised dots to be distinguished with the other physical button. In some embodiments, the touch button includes a capacitive touch key, a resistive touch key or a touch screen. When the keying is the touch key, different keys have different labels to make a distinction, for example, a color label, graphics label.

The key unit is configured to output a selection instruction indicating at least one working mode, where the at least one working mode is selected from a group consisting of a basal rate delivery mode, a programmable basal rate delivery mode, an delivery suspend mode, a system locking mode and a wireless control mode. In some embodiments, the key unit may be more than one. That is, each key unit has a prestored working mode, for example, a key unit with prestored basal rate delivery mode, a key unit with programmable basal rate delivery mode prestored based on actual situation of the patient.

Figure 8:
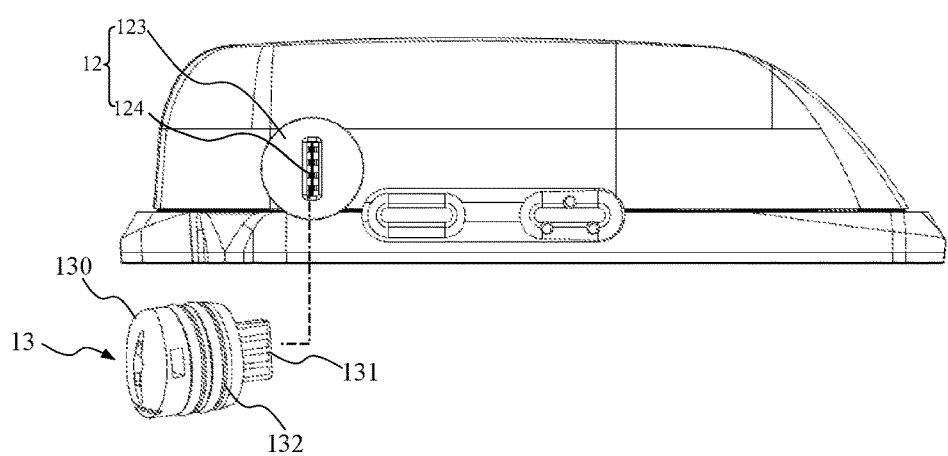
FIG. 8 illustrates a schematic diagram of a key and a socket of a disposable tubeless fluid delivery system according to an embodiment of the present disclosure.

In some embodiments, the key unit includes a key 13 and a first socket 12. Referring to FIG. 8, a schematic diagram of a key and a first socket of a disposable tubeless fluid delivery system according to an embodiment of the present disclosure is illustrated.

Figure 9:
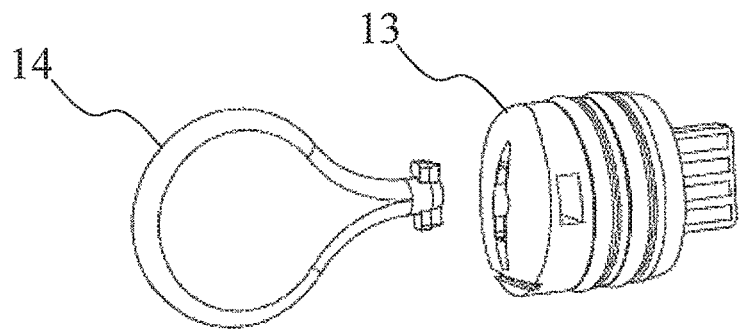
FIG. 9 to FIG. 11 illustrate a separated a handle and a key, a combined a handle and a key and a handle and a key that they are being used.
Figure 10:
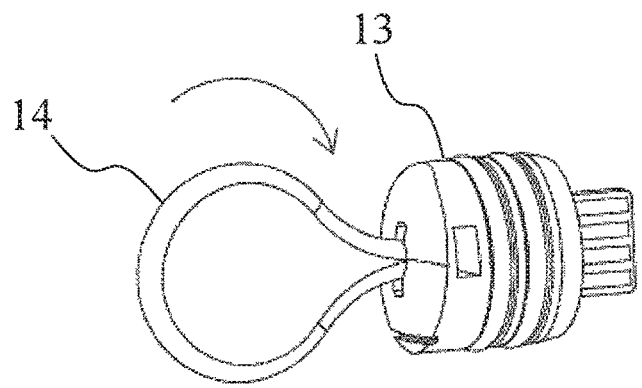
Figure 11:
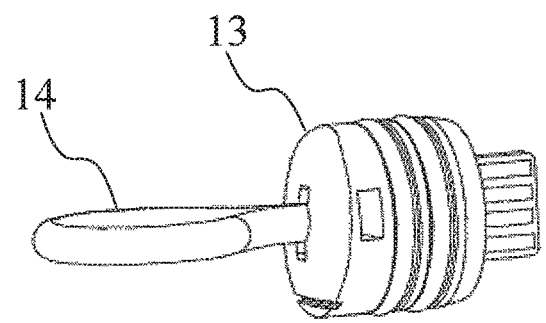

In order to wear or manage, the key 13 further includes a handle 14 configured to combine and separate the key 13 and the first socket 12. Referring to FIG. 9 to FIG. 11, a separated handle 14 and key 13, a combined handle 14 and key 13 and a handle 14 and a key 13 that they are being used are illustrated.

In some embodiments, the key 13 includes a key shell 130 and a first plug 131 embedded in the key shell 130, the key shell 130 has a built-in electric circuit located inside the key shell 130, where a first portion of the first plug 131 is embedded in the key shell 130 and a second portion of the first plug 131 protrudes out of the key shell 130, and the first socket 12 comprises a first groove 123 with a first slot 124 disposed on a bottom of the first groove 123, where a side wall of the first groove 123 surrounds the first slot 124, the second portion of the first plug 131 is configured to be inserted into the first slot 124 from an opening side of the first groove 123 and the key shell 130 is configured to contact with the side wall of the first groove 123. Specifically, the built-in electric circuit is an analog circuit including electric resistances, electric capacities or a combination thereof, or a digital integrated circuit including Flash, EEROM, or one-time DATA BURNING type memory device, or a digital integrated circuit with identity recognition function, or a digital integrated circuit with an authentication function, an encryption function or a combination thereof, or a digital-analog hybrid integrated circuit. The built-in electric circuit is set on the printed circuit board (PCB).

Figure 12:
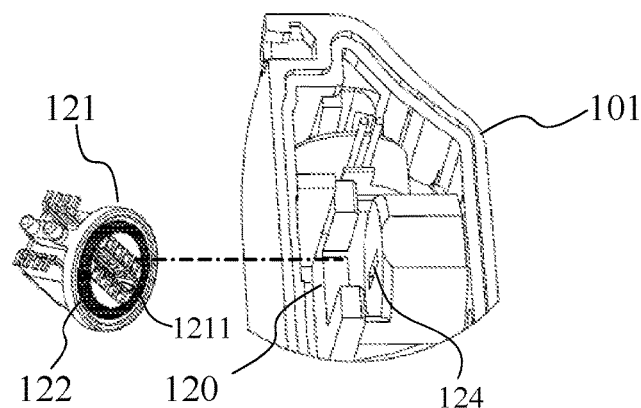
FIG. 12 illustrates an enlarged view in section on B of FIG. 6.

Referring to FIG. 12, an enlarged view in section on B of FIG. 6 is illustrated. As shown in FIG. 12, the first socket 12 further includes a second slot 120 disposed on a side of the first groove 123 (as shown in FIG. 8) opposite to the opening side and a first connector 121 set in the second slot 120, where the first connector 121 is used to be electrically connected with the control unit, and the first connector 121 is also electrically connected with the built-in electric circuit set on PCB. When the key 13 is inserted into the first socket 12, the first plug 131 is inserted into the first connector 121 and thus electrically connected with the first connector 121, and then which realizes communication between the key 13 and the control unit. In order to achieve waterproof, a second O-shaped sealing ring 132 is set on the key shell 130. A first O-shaped sealing ring 122 is set on a surface on which the first connector 121 is attached with the first socket 12. When the key 13 is inserted into the first socket 12, the second O-shaped sealing ring 132 on the key shell 130 and the first socket 12 fit tightly to achieve waterproof seal, while the first O-shaped sealing ring 122 on the first connector 121 and a socket surface opposite to it fit tightly to achieve waterproof seal.

Figure 13:
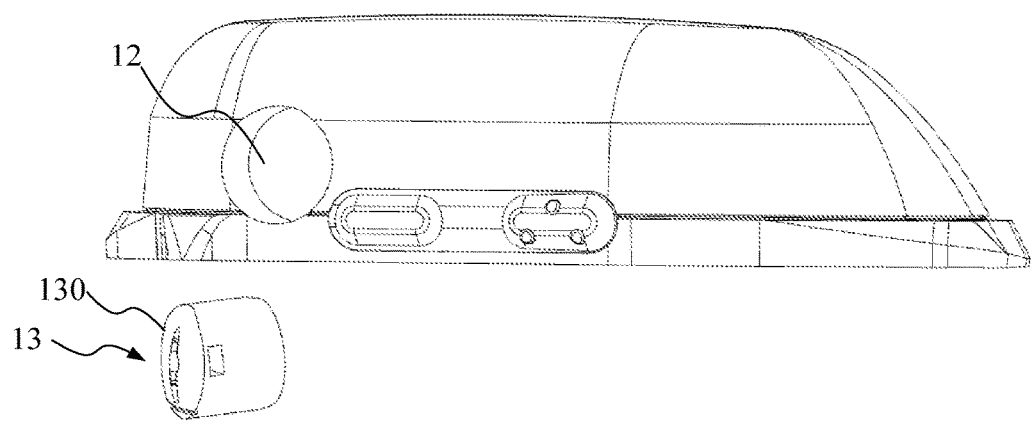
FIG. 13 illustrates a schematic diagram of a key and a socket of a disposable tubeless fluid delivery system according to another embodiment of the present disclosure.

Referring to FIG. 13, a schematic diagram of a key and a socket of a disposable tubeless fluid delivery system according to another embodiment of the present disclosure illustrated. As shown in FIG. 13, the socket 12 is a sealed groove, and the key 13 is a sensing key, the sensing key includes the key shell 130 and a sensor circuit located inside the key shell 130. Therefore, the key 13 and the control unit embedded in the disposable tubeless fluid delivery system may realize non-raised dots communication. Specifically, the sensor circuit is includes a magnetic sensor circuit, an optical sensor circuit, a NFC tag circuit or a RFID tag circuit.

The fluid reservoir unit is configured to store a fluid. In some embodiments, the fluid is insulin used for treatment of diabetic. But it is not limited to insulin, and the fluid stored in the fluid reservoir unit may be different based on the actual need of patient.

The indwelling unit is configured to let through the fluid to a patient when it is implanted in a subcutaneous tissue of the patient, where the indwelling unit includes an indwelling cannula configured to be implanted in the subcutaneous tissue of the patient. In some embodiments, the indwelling cannula is implanted in a subcutaneous tissue in the patient via the aid of a steel needle. Specifically, when the indwelling cannula covers the steel needle, the inside of the steel needle is hollow; when the steel needle is a groove steel needle, the indwelling cannula is set in the groove of the groove steel needle; similarly, the steel needle may also be a steel needle with an inner chamber, when the inner chamber is used as a termination of delivering drug termination.

The fluid driving unit is configured to deliver the drug fluid stored in the fluid reservoir unit to the subcutaneous tissue of the patient by the indwelling unit, when it receives a delivery instruction. In some embodiments, the fluid driving unit includes an ejection device and a subcutaneous hose installation device, which are configured to implant the indwelling cannula of the indwelling unit into the skin of the patient. When the indwelling cannula is implanted, the subcutaneous cannula installation device uses steel needle to puncture the skin of the patient by the ejection device and implants the indwelling cannula in the subcutaneous tissue of the patient, and then the steel needle is pulled out by a return pin device, so the fluid stored in the fluid reservoir unit is delivered to the subcutaneous tissue of the patient through the indwelling unit.

In some embodiments, the disposable tubeless fluid delivery system further includes a glucose sensor configured to dynamically monitor glucose level and a glucose monitoring module configured to process effective glucose signals output by the glucose sensor, where the glucose sensor is integrated in the indwelling unit, the glucose monitoring module is integrated in the control unit connected to the indwelling unit. In some embodiments, the glucose sensor is set on an outside surface of the indwelling cannula, and the glucose monitoring module is set in the shell of the disposable tubeless fluid delivery system, but it is not limited to the embodiments disclosed, other means should also apply to the present disclosure, other means includes any means which can realize combination of the glucose sensor and the indwelling unit, and realize combination of the glucose monitoring module and the control unit connected to the indwelling unit.

The control unit is respectively coupled to the button unit, the key unit, the fluid reservoir unit, the indwelling unit and the fluid driving unit, where the control unit is configured to, when it receives the button-pressing instruction, the selection instruction of the working mode, or a combination thereof, output the corresponding delivery instruction to the fluid driving unit, so as to control the fluid driving unit to deliver the fluid or suspend fluid delivery. In some embodiments, the control unit is prestored various button-pressing instructions and working mode set corresponding to the key unit, where the working mode includes a basal rate delivery mode, a programmable basal rate delivery mode, an delivery suspend mode, a system locking mode and a wireless control mode. The control unit may be a single chip, or other microprocessor, which is configured to receive, transmit and return signal of all units, and coordinate and manage all units, for example, it may manage amount of the fluid stored in the fluid reservoir unit, when the amount of the fluid is insufficient, it outputs a reminder and an alarm, or when the device breaks down. The control unit also manages the functional module such as a wireless transmission module, power supply module.

In an optional embodiment, a buzzer cavity is set in a shell of the disposable tubeless fluid delivery system, a buzzer is set in the buzzer cavity, where the buzzer is configured to produce a buzz to sound an alarm, a reminder, or a combination thereof, and the buzzer is also configured to transmit ultrasonic data. The buzzer is connected to the control unit via a wire or a contact. In response to the user's instruction, or when the fluid stored in the pump base 102 runs out, or the device breaks down, the buzzer may remind, alarm or transmit data by ultrasound.

In an optional embodiment, a groove is set in the shell of the disposable tubeless fluid delivery system, and a vibration motor is set in the groove, where the vibration motor is connected to the control unit by a wire or a contact. In response to the user's instruction, or when the fluid stored in the pump base 102 runs out, or the device breaks down, the vibration motor may remind user to do next step operation or alarm.

In an optional embodiment, the disposable tubeless fluid delivery system further includes an indicator light, a transparent portion is correspondingly set in the shell of the disposable tubeless fluid delivery system, the indicator light indicates a system state by flashing through the transparent portion and reminds user.

As is mentioned above, referring to FIG. 3, when the disposable tubeless fluid delivery system 1 includes the separable controller 101 and pump base 102, the control unit, the button unit and the key unit are set on the controller 101. the fluid reservoir unit, and the fluid driving unit and the indwelling unit are set on the pump base 102.

Figure 14:
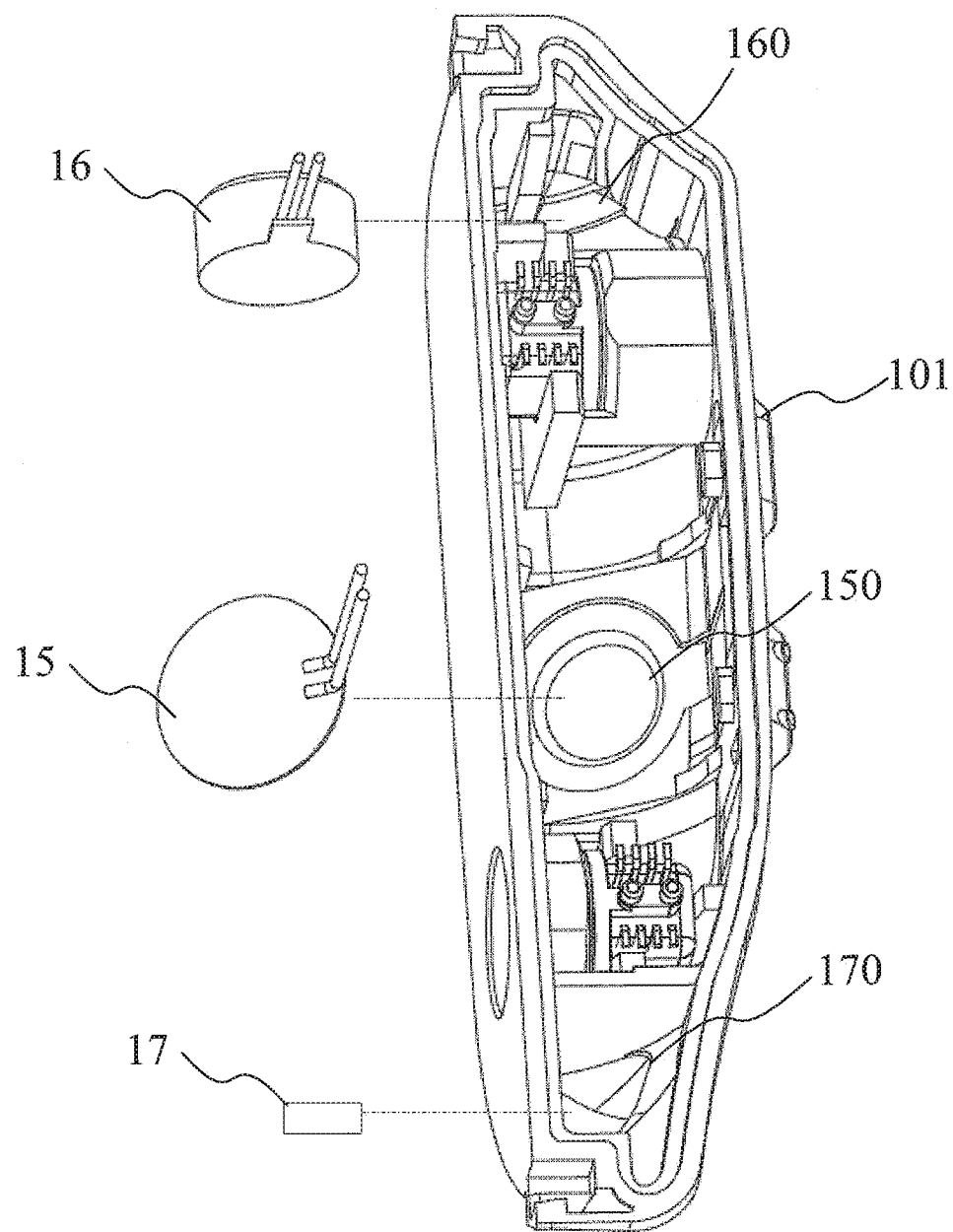
FIG. 14 to FIG. 15 illustrate schematic structure diagrams of a controller with a buzzer, a vibration motor and an indicator light of a disposable tubeless fluid delivery system according to an embodiment of the present disclosure.
Figure 15:
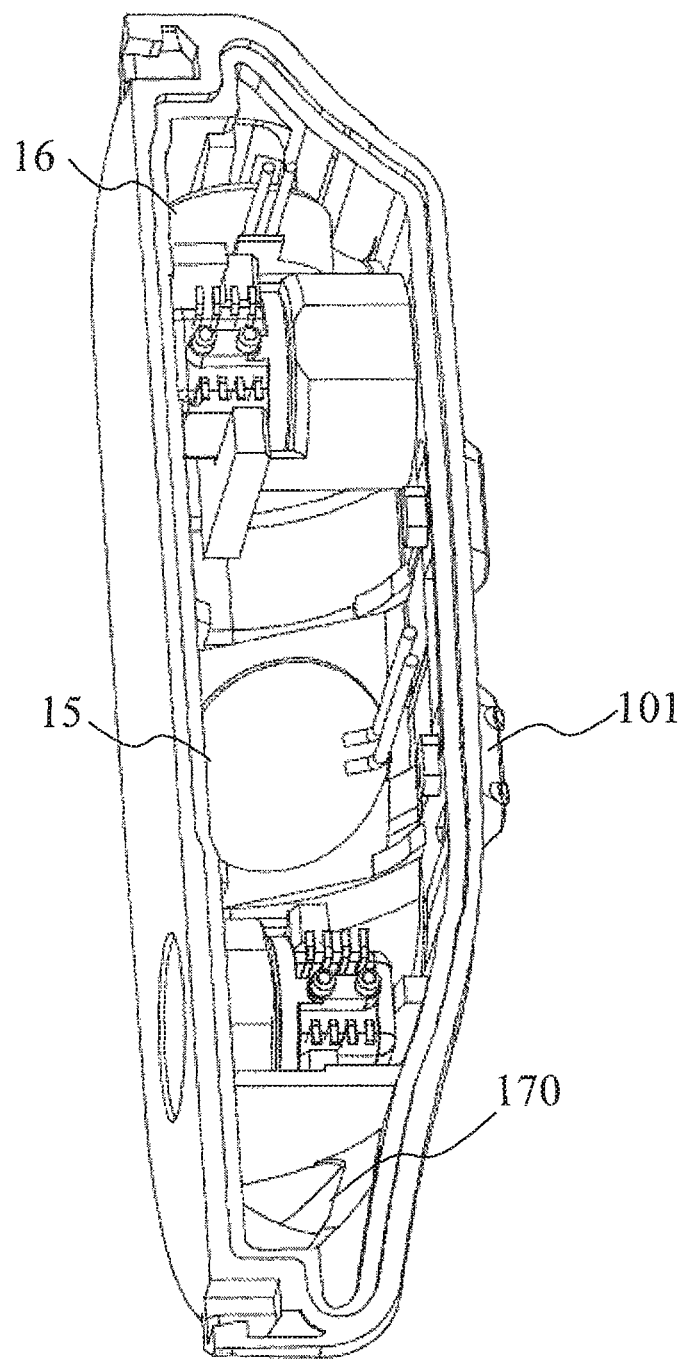

Referring to FIG. 14 to FIG. 15, schematic structure diagrams of a controller with a buzzer, a vibration motor and an indicator light of a disposable tubeless fluid delivery system according to an embodiment of the present disclosure are illustrated. As shown in FIG. 14 and FIG. 15, in some embodiments, when the disposable tubeless fluid delivery system includes the controller 101 and the pump base 102 connected to the controller 101 or separated from the controller 101, a first buzzer cavity 150 is set on the shell of the controller 101, and a first buzzer 15 is set in the first buzzer cavity 150, where the first buzzer 15 is connected to a control unit electric circuit of the controller 101 via the wire.

Figure 16:
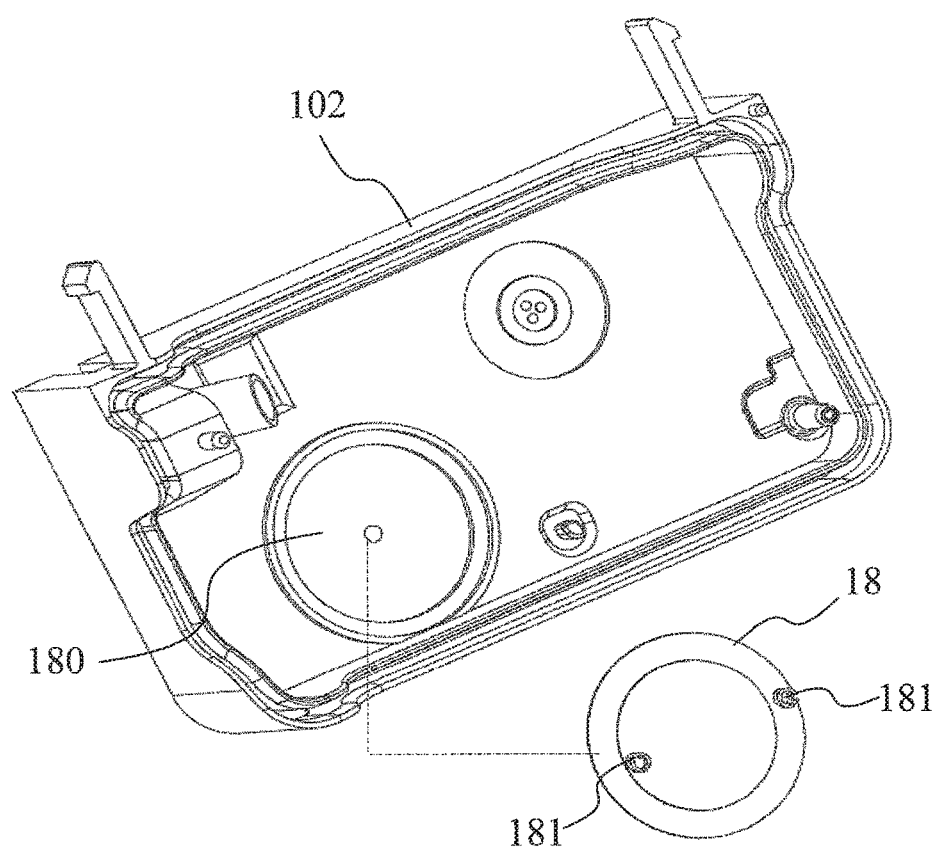
FIG. 16 to FIG. 17 illustrate schematic structure diagrams of a pump base with a buzzer of a disposable tubeless fluid delivery system according to an embodiment of the present disclosure.
Figure 17:
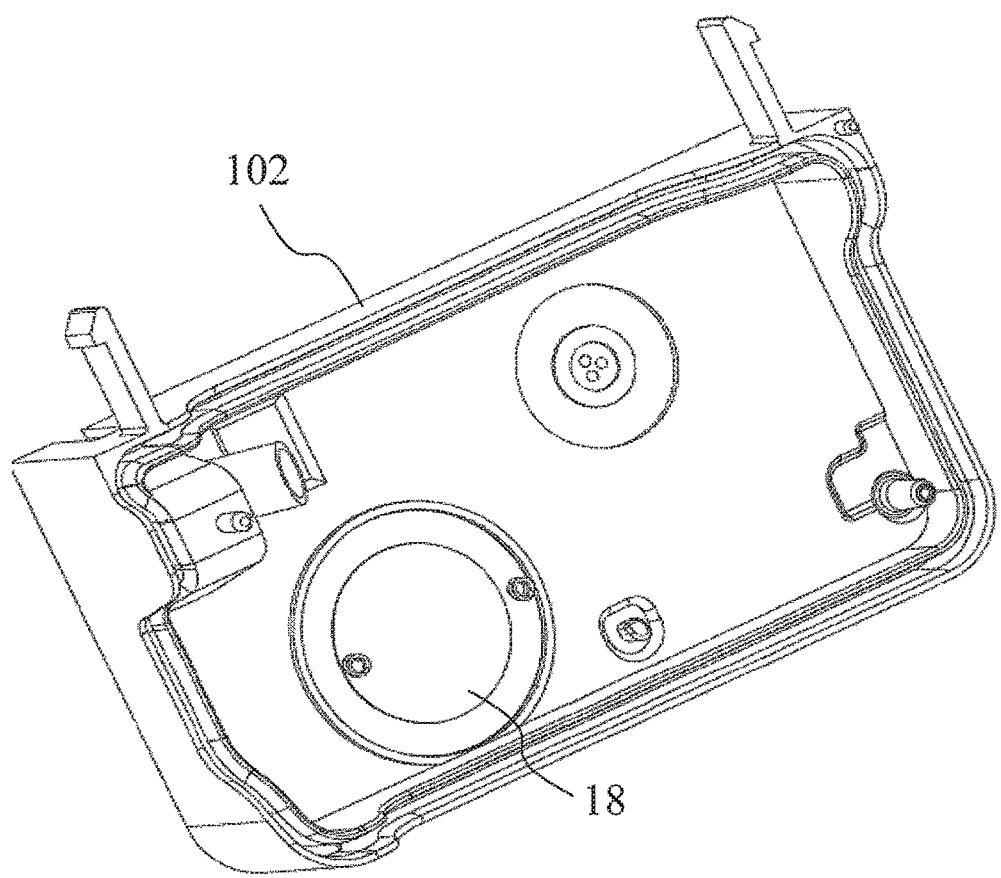

Referring to FIG. 16 to FIG. 17, schematic structure diagrams of a pump base with a buzzer of a disposable tubeless fluid delivery system according to an embodiment of the present disclosure are illustrated. A second buzzer cavity 180 is set on the shell of the pump base 102, and a second buzzer 18 is set in the second buzzer cavity 180, where the second buzzer 18 is connected to the built-in electric circuit of the pump base 102 via the contact 181.

A second groove 160 is set in the shell of the controller 101, and the vibration motor 16 is set in the second groove 160, where the vibration motor 16 is connected to the control unit via the wire. In response to the user's instruction, or when the fluid stored in the pump base 102 runs out, or the device breaks down, the vibration motor 16 may remind user to do next step operation or alarm.

The indicator light 17 is set in the shell of the controller 101, a transparent portion 170 is correspondingly set on the shell of the controller 101, the indicator light 17 indicates a system state by flashing through transparent portion and reminds user.

In summary, the disposable tubeless fluid delivery system provided in the present disclosure uses independent control structure to enhance convenience of using and wearing. That is, the control unit, the button unit and the key unit are set in one device, where the control unit is configured to process an instruction given by a user, and coordinate and manage the device operation, while the button unit and the key unit are configured to realize communications between the user and the device. Furthermore, setting the button and the key on the device realizes the fluid delivery and completes treatment for a patient under the cooperations of the buzzer, the vibration motor and the indicator light. In some embodiments, the indwelling unit is combined with the glucose sensor, and the control unit is combined with the glucose monitoring module. As such, the disposable tubeless fluid delivery system can realize both glucose monitoring and fluid delivery, so as to complete treatment for the patient. Specifically, when the patient is being treated, he/she sticks the whole device to his/her skin, and sets up a program of fluid delivery by the button unit and/or the key unit. In response to the user's instruction, or when the fluid stored in the pump base runs out, or the device breaks down, the disposable tubeless fluid delivery system will remind the user to do the next step operation by using the buzzer, the vibration motor, the indicator light, or a combination thereof. The present disclosure overcomes the various shortcomings of the current technology and has high industrial utilization value.

The above descriptions of the detailed embodiments are only to illustrate the principle and the effect of the present disclosure, and it is not to limit the scope of the present disclosure. Those skilled in the art can modify or change the embodiments without departing from the spirit and scope of the present disclosure. Accordingly, all equivalent modifications and variations completed by persons of ordinary skill in the art, without departing from the spirit and technical idea of the present disclosure, should fall within the scope of the present disclosure defined by the appended claims.

What is claimed is:

1. A disposable tubeless fluid delivery system, comprising:
   a button unit configured to receive instructions given by a user through pressing button;
   a key unit configured to output a selection instruction indicating at least one working mode, wherein the at least one working mode is selected from a group including a basal rate delivery mode, a programmable basal rate delivery mode, a delivery suspend mode, a system locking mode and a wireless control mode;
   a fluid reservoir unit configured to store a fluid;
   an indwelling unit configured to let through the fluid to a patient when it is implanted in a subcutaneous tissue of the patient, wherein the indwelling unit comprises an indwelling cannula configured to be implanted in the subcutaneous tissue of the patient;
   a fluid driving unit configured to deliver the fluid stored in the fluid reservoir unit to the subcutaneous tissue of the patient via the indwelling unit, when it receives a delivery instruction; and
   a control unit coupled to the button unit, the key unit, the fluid reservoir unit, the indwelling unit and the fluid driving unit, wherein the control unit is configured to, when it receives a button-pressing instruction, the selection instruction of the working mode, or a combination thereof, output the corresponding delivery instruction to the fluid driving unit, so as to control the fluid driving unit to deliver the fluid or suspend fluid delivery;
   wherein the key unit comprises a plurality of keys (13) and a first socket (12), each of the plurality of keys (13) comprises a key shell (130), a built-in electric circuit located inside the key shell (130), and a first plug (131), where a first portion of the first plug (131) is embedded in the key shell (130) and a second portion of the first plug (131) protrudes out of the key shell (130), and the first socket (12) comprises a first groove (123) with a first slot (124) disposed on a bottom of the first groove (123), where a side wall of the first groove (123) surrounds the first slot (124), the second portion of the first plug (131) is configured to be inserted into the first slot (124) from an opening side of the first groove (123) and the key shell (130) is configured to contact with the side wall of the first groove (123), and the first socket (12) further comprises a second slot (120) disposed on a side of the first groove (123) opposite to the opening side and a first connector (121) set in the second slot (120), where the first connector (121) is configured to be electrically connected with the built-in electric circuit when the each of the plurality of keys (13) is inserted into the first socket (12).

2. The disposable tubeless fluid delivery system according to claim 1, wherein the button unit comprises physical buttons, touch buttons, or a combination thereof.

3. The disposable tubeless fluid delivery system according to claim 2, wherein the physical buttons comprise a first physical button configured to set the fluid dose, and a second physical button configured to input a confirmation instruction wherein one of the first and second physical buttons is provided with raised dots to be distinguished from the other physical button.

4. The disposable tubeless fluid delivery system according to claim 1, wherein the built-in electric circuit is an analog circuit comprising electric resistances, electric capacities or a combination thereof, or a digital integrated circuit including Flash, EEROM, or one-time DATA BURNING type memory device, or a digital integrated circuit with identity recognition function, or a digital integrated circuit with an authentication function, an encryption function or a combination thereof, or a digital-analog hybrid integrated circuit.

5. The disposable tubeless fluid delivery system according to claim 1, wherein a first O-shaped sealing ring (122) is set on a surface on which the first connector (121) is attached with the first groove (123) of the first socket (12), a second O-shaped sealing ring (132) is circumferentially disposed on the key shell (130), and the second O-shaped sealing ring (132) on the key shell (130) and the side wall of the first groove (123) of the first socket (12) fit tightly to achieve a waterproof seal.

6. The disposable tubeless fluid delivery system according to claim 1, wherein each of the plurality of keys (13) further comprises a handle (14) configured to combine and separate the each of the plurality of keys (13) and the first socket (12).

7. The disposable tubeless fluid delivery system according to claim 1, wherein at least one buzzer cavity is set in a shell of the disposable tubeless fluid delivery system, at least one buzzer is set in the at least one buzzer cavity, wherein the at least one buzzer is configured to produce a buzz to sound an alarm, a reminder, or a combination thereof, and the at least one buzzer is also configured to transmit ultrasonic data.

8. The disposable tubeless fluid delivery system according to claim 7, wherein the at least one buzzer is connected to the control unit via a wire or a contact.

9. The disposable tubeless fluid delivery system according to claim 1, wherein a second groove (160) is set in a shell of the disposable tubeless fluid delivery system and a vibration motor (16) is disposed in the second groove (160), where the vibration motor (16) is connected to the control unit via a wire.

10. The disposable tubeless fluid delivery system according to claim 1, wherein the disposable tubeless fluid delivery system further comprises an indicator light (17) having a transparent portion (170) that is correspondingly set on the shell of the disposable tubeless fluid delivery system, such that the indicator light (17) indicates a system state by flashing through the transparent portion (170).

11. The disposable tubeless fluid delivery system according to claim 1, further comprising a glucose sensor configured to dynamically monitor glucose level and a glucose monitoring module configured to process effective glucose signals output by the glucose sensor, wherein the glucose sensor is integrated in the indwelling unit and the glucose monitoring module is integrated in the control unit connected to the indwelling unit.

12. The disposable tubeless fluid delivery system according to claim 1, further comprising a controller (101) and a pump base (102) connected to the controller (101), wherein the control unit, the button unit and the key unit are set on the controller (101), and the fluid reservoir unit, the fluid driving unit, and the indwelling unit are set on the pump base (102).

13. The disposable tubeless fluid delivery system according to claim 12, wherein the controller (101) and the pump base (102) are separable components.

14. The disposable tubeless fluid delivery system according to claim 13, wherein the controller (101) and the pump base (102) are combined by a snap hook socket or a third groove (1011) and a snap hook (1022).

15. The disposable tubeless fluid delivery system according to claim 14, further comprising a releasing key for separating the snap hook (1022) from the snap hook socket or the third groove (1011).

16. The disposable tubeless fluid delivery system according to claim 13, wherein the controller (101) and the pump base (102) are electrically connected by a second socket (1010) disposed on the controller (101) and a second plug (1024) disposed on the pump base (102).

17. The disposable tubeless fluid delivery system according to claim 1, wherein the second portion of the first plug (131) is further configured to be inserted into the first connector (121) and to be electrically connected with the first connector (121), when the each of the plurality of keys (13) is inserted into the first socket (12).

18. The disposable tubeless fluid delivery system according to claim 17, wherein the first connector (121) comprises a third slot (1211) configured to receive the second portion of the first plug (131).

19. The disposable tubeless fluid delivery system according to claim 1, wherein the first connector (121) is configured to be electrically connected with the control unit.

20. The disposable tubeless fluid delivery system according to claim 6, wherein the handle (14) is configured to be combined with or separated from the key shell (130), when the handle (14) is combined with the key shell (130), one end of the handle (14) is embedded in the key shell (130), the other end of the handle (14) protrudes out of the key shell (130) so as to be handled by a user; and the handle (14) is further configured to be rotated by a user so as to control the separation and combination of the handle (14) and the key shell (130).

21. The disposable tubeless fluid delivery system according to claim 16, wherein the second socket (1010) comprises a second connector (1014) and a connector position groove (1013), where the second connector (1014) is configured to be electrically connected with the control unit; and
the second plug (1024) comprises a plug body (1025) and a plug end (1020) embedded in the plug body (1025), and the second plug (1024) is configured to be inserted into the second socket (1010) and to be electrically connected with the second connector (1014).

22. The disposable tubeless fluid delivery system according to claim 21, wherein a third O-shaped sealing ring (1015) is disposed on a fitting surface of the second connector (1014) and the second socket (1010), a fourth O-shaped sealing ring (1021) is disposed on the plug body (1025) and the fourth O-shaped sealing ring (1021) and a side wall of the second socket (1010) fit tightly to achieve a waterproof seal.

* * * * *